US012083360B2

(12) United States Patent
Noack et al.

(10) Patent No.: US 12,083,360 B2
(45) Date of Patent: Sep. 10, 2024

(54) FIN FOR COLLIMATING THERAPEUTIC RADIATION

(71) Applicant: Siemens Healthineers AG, Forchheim (DE)

(72) Inventors: Olivia Noack, Bayreuth (DE); Sebastian Graebner, Speichersdorf (DE); Georg Walberer, Kastl (DE); Michael Langguth, Wipfratal (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/891,181

(22) Filed: Aug. 19, 2022

(65) Prior Publication Data

US 2023/0069701 A1 Mar. 2, 2023

(30) Foreign Application Priority Data

Aug. 24, 2021 (DE) ..................... 10 2021 209 248.9

(51) Int. Cl.
*A61N 5/10* (2006.01)
(52) U.S. Cl.
CPC .... *A61N 5/1045* (2013.01); *A61N 2005/1092* (2013.01)
(58) Field of Classification Search
None
See application file for complete search history.

(56) References Cited

U.S. PATENT DOCUMENTS

| 5,343,048 | A | 8/1994 | Pastyr | |
|---|---|---|---|---|
| 6,459,769 | B1* | 10/2002 | Cosman | G21K 1/04 378/65 |
| 6,526,123 | B2* | 2/2003 | Ein-Gal | G21K 1/04 378/65 |
| 2005/0185766 | A1 | 8/2005 | Tsujita | |
| 2007/0127624 | A1 | 6/2007 | Seeber et al. | |
| 2015/0206613 | A1* | 7/2015 | Echner | A61N 5/1045 250/515.1 |
| 2017/0148536 | A1 | 5/2017 | Kawrykow et al. | |

FOREIGN PATENT DOCUMENTS

| DE | 4203610 C1 | 8/1993 |
|---|---|---|
| DE | 10211492 A1 | 10/2003 |

* cited by examiner

*Primary Examiner* — Marcus H Taningco
(74) *Attorney, Agent, or Firm* — Harness, Dickey & Pierce, P.L.C.

(57) ABSTRACT

One or more example embodiments of the present invention relates to a fin for collimating therapeutic radiation. The fin comprises a collimation area made of a first material and a holding area made of a second material. Herein, the collimation area and the holding area are soldered together. Herein, the first material is formed to collimate therapeutic radiation. Herein, the holding area can be coupled to an adjustment device for adjusting the fin.

19 Claims, 3 Drawing Sheets

FIN FOR COLLIMATING THERAPEUTIC RADIATION

CROSS-REFERENCE TO RELATED APPLICATION(S)

The present application claims priority under 35 U.S.C. § 119 to German Patent Application No. 102021209248.9, filed Aug. 24, 2021, the entire contents of which are incorporated herein by reference.

FIELD

One or more example embodiments of the present invention relates to a fin for collimating therapeutic radiation. One or more example embodiments of the present invention further relates to a collimator and a method for manufacturing a fin for collimating therapeutic radiation.

BACKGROUND

It is known to perform radiotherapy, for example, to treat a tumor or also to treat a benign disease such as, for example, heel spurs, tennis elbow, shoulder pain, arthrosis of the various joints or vertebral hemangiomas. Herein, therapeutic radiation is emitted onto a treatment area of an examination object, for example the tumor or the affected limbs. Herein, therapeutic radiation can in particular be high-energy electromagnetic radiation, in particular X-radiation, generated with a linear accelerator. Alternatively, therapeutic radiation can be particle radiation, in particular proton radiation or heavy ion radiation or alpha radiation etc.

Herein, an area that can be irradiated is delimited by a radiation field of the therapeutic radiation. In order to protect surrounding tissue and/or organs of the examination object within the radiation field but outside the treatment area from therapeutic radiation, therapeutic radiation is collimated during radiotherapy. For this purpose, a plurality of fins is typically arranged or aligned in the radiation field between a source of the therapeutic radiation and the examination object such that only the treatment area to be irradiated in the radiation field is not covered by any of the fins. Herein, one of the plurality of fins is formed to attenuate or absorb the therapeutic radiation to such an extent that radiation exposure or the intensity of therapeutic radiation behind the fin is negligibly low. Herein, "behind" describes the arrangement as seen from the source of the therapeutic radiation. In particular, the examination object is arranged "behind" the fin. Thus, in particular, the area of the fin positioned in the radiation field of the therapeutic radiation, hereinafter referred to as the collimation area, must be made of a material that attenuates the therapeutic radiation. For this purpose, the fin typically consists of tungsten or a compound comprising tungsten or tungsten compound.

In order to be able to arrange or adjust the fin precisely, the fin typically comprises a holding area with which the fin can be coupled to an adjustment device. Herein, the adjustment device is formed to arrange or adjust the fin, and thus in particular the collimation area, precisely in the radiation field.

In order to ensure sufficient precision when adjusting or positioning or arranging the fin and sufficient coverage of healthy tissue and/or organs of the examination object, in some applications, the fins have to be produced to an accuracy of 5 μm. In particular, in some applications, the fins have to be produced to an accuracy of 0.2 μm. This is typically achieved by cutting out the fin from a block by wire erosion. Herein, a fin is typically 2-3 mm thick. The thickness of the fin describes the extension of the fin in a direction perpendicular to the beam direction of the therapeutic radiation. The extension of the fin perpendicular to the thickness and parallel to the beam direction is described by the height of the fin.

Due to its properties, tungsten is difficult to join to other materials. In particular, tungsten has a lower coefficient of thermal expansion or thermal coefficient than steel or copper, for example. In order to prevent the introduction of heat, for example due to wire erosion of the fin, from causing stresses in the fin, the fin is typically made of one single material, the material of the collimation area, in particular tungsten or a tungsten compound.

US 2017/0148536 A1 describes a fin with which the holding area of the fin comprises a frame around the collimation area in which a tungsten plate is enclosed. For this purpose, the individual parts, the holding area including the frame and the tungsten plate, must first be produced individually and then joined. Joining at the end of the manufacturing of the fin does not allow the above-described requirements for accuracy to be met. Reworking is not possible in this case.

SUMMARY

Typically both the collimation area and the holding area of the fin are made of the same material, in particular tungsten or a tungsten compound. However, it is not necessary also to produce the holding area from tungsten or a tungsten compound, since the holding area is not arranged in the beam path and does not have to be formed to attenuate therapeutic radiation. Since tungsten is a very expensive material, there is great interest in producing only the collimation area from tungsten or a tungsten compound.

According to one or more example embodiments, a fin has a holding area made of a different material than the collimation area.

According to one or more example embodiments, a fin for collimating therapeutic radiation includes a collimation area including a first material; and a holding area including a second material, wherein the collimation area and the holding area are soldered together, the first material is configured to collimate therapeutic radiation, and the holding area is couplable to an adjustment device for adjusting the fin.

According to one or more example embodiments, the first material and the second material are hard-soldered together.

According to one or more example embodiments, the first material and the second material are paramagnetic.

According to one or more example embodiments, the first material is tungsten or a compound comprising tungsten.

According to one or more example embodiments, the second material comprises titanium or stainless steel.

According to one or more example embodiments, the holding area and the collimation area are soldered together with a copper solder, a gold solder, a silver solder or a titanium solder.

According to one or more example embodiments, the compensating layer is between the first material and the second material, and the compensating layer is formed from a compensating material, the compensating material compensates for a difference in coefficients of thermal expansion of the first material and the second material, respectively.

According to one or more example embodiments, the compensating layer is formed by a copper plate.

According to one or more example embodiments, the compensating layer is formed by a net-like element and a solder, and the net-like element includes nickel.

According to one or more example embodiments, the fin further includes a guide element, wherein the guide element is formed by the first material and the second material.

According to one or more example embodiments, a collimator includes a plurality of fins, each of the plurality of fins including, a collimation area including a first material, and a holding area including a second material, wherein the collimation area and the holding area are soldered together, the first material is configured to collimate therapeutic radiation, and the holding area is couplable to an adjustment device for adjusting the fin; and the collimator further includes the adjustment device, wherein the respective holding areas of the fins are coupled to the adjustment device, and the adjustment device is configured to adjust each fin of the plurality of fins perpendicular to a contact surface of the holding area and the collimation area.

According to one or more example embodiments, a method for manufacturing the fin according to one or more example embodiments includes soldering together a first block including the first material and a second block including the second material to form a combination block.

According to one or more example embodiments, the method further includes cutting out the fin from the combination block by wire erosion.

According to one or more example embodiments, the method further includes milling out at least one side surface of the fin from the combination block.

According to one or more example embodiments, the soldering includes introducing a compensating layer between the contact surfaces of the first block and the second block.

According to one or more example embodiments, the method further includes at least one of (i) milling out at least one guide element from the combination block, or (ii) milling out a contour of the holding area from the combination block.

BRIEF DESCRIPTION OF THE DRAWINGS

Features and advantages will become clear and more plainly comprehensible in the conjunction with the following figures and the description thereof. Herein, the figures and descriptions are not intended to limit the present invention and its embodiments in any way.

In different figures, the same components are given the same reference symbols. The figures are not generally true to scale.

In the figures:

FIG. 1 shows an exemplary embodiment of a fin for collimating therapeutic radiation, FIG. 2 shows an exemplary embodiment of a collimator, FIG. 3 shows a first exemplary embodiment of a method for manufacturing a fin for collimating therapeutic radiation, and FIG. 4 shows a second exemplary embodiment of a method for manufacturing a fin for collimating therapeutic radiation.

DETAILED DESCRIPTION

Figure 1:
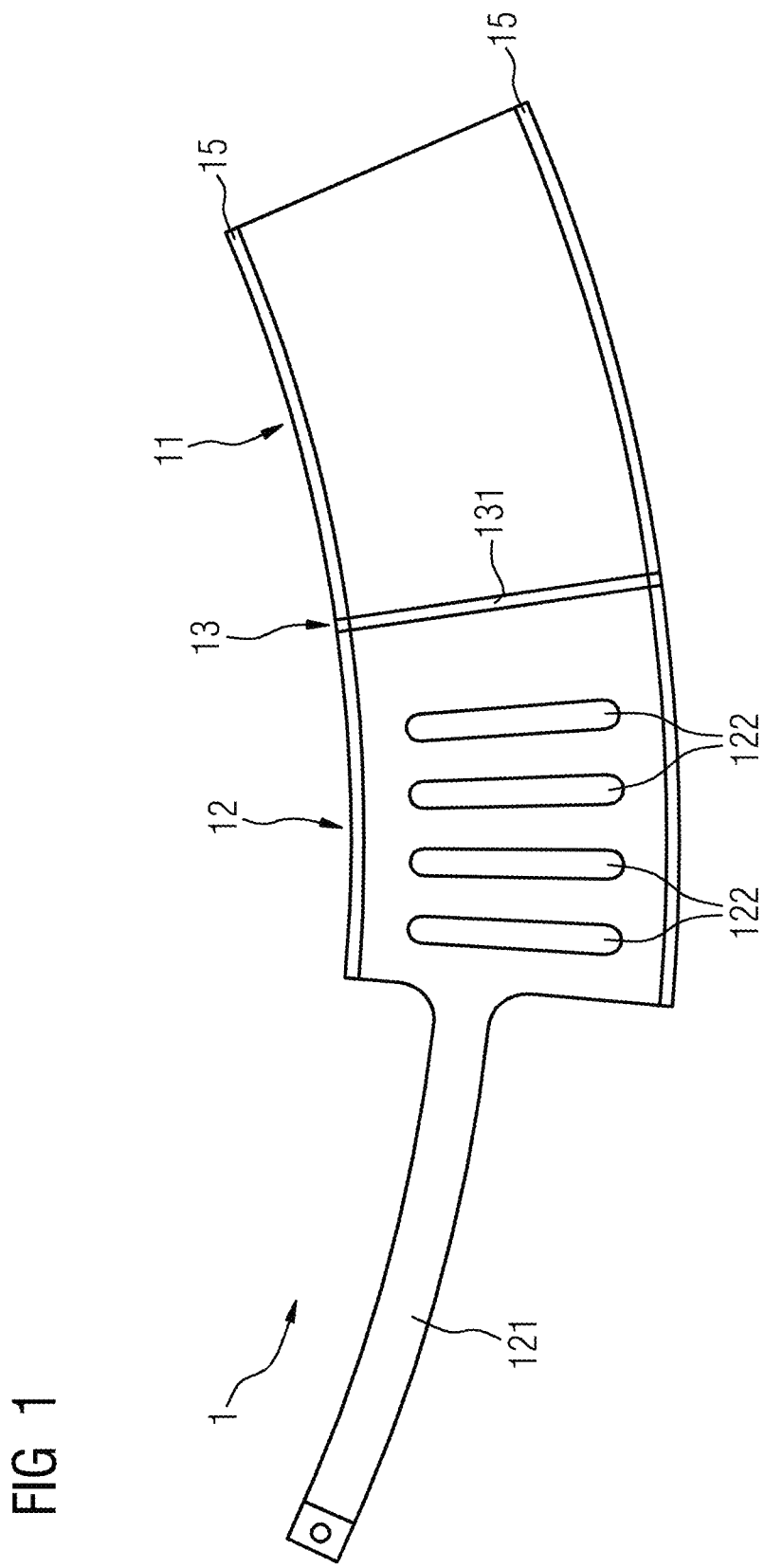

The following describes one or more example embodiments of the present invention with respect to the claimed apparatuses and with respect to the claimed method. Features, advantages or alternative embodiments mentioned in this regard are equally applicable to the other claimed subject matter and vice versa. In other words, the physical claims (which are, for example, directed at an apparatus) can also be developed with the features described or claimed in connection with a method. Herein, the corresponding functional features of the method are formed by corresponding physical modules.

One or more example embodiments of the present invention relates to a fin for collimating therapeutic radiation. The fin comprises a collimation area made of a first material and a holder area made of a second material. Herein, the collimation area and the holder area are soldered together. Herein, the first material is formed to collimate therapeutic radiation. Herein, the holding area can be coupled to an adjustment device for adjusting the fin.

In a particularly preferred embodiment of the present invention, the therapeutic radiation is X-radiation. X-radiation describes electromagnetic radiation with an energy of more than 100 eV. X-radiation can in particular be collimated for radiotherapy. In radiotherapy, a treatment area of an examination object is irradiated with ultra-hard or ultra-high-energy X-radiation (>1 MeV). In particular, the treatment area can be irradiated with X-radiation with an energy greater than or equal to 6 MeV.

In an alternative embodiment, the therapeutic radiation for radiotherapy can be particle radiation, in particular proton radiation or heavy ion radiation or alpha radiation etc.

In radiotherapy, it is, for example, possible to treat tumors or heel spurs, tennis elbow, shoulder pain, arthrosis of the various joints, vertebral hemangiomas etc. by irradiation with therapeutic radiation. For this purpose, the examination object, in particular a patient, is positioned in a radiation field of the therapeutic radiation. Herein, the examination object can in particular be a human or an animal. Herein, the examination object is positioned in such a way that an area to be treated or treatment area is arranged in the radiation field. The radiation field describes an area that can be irradiated with therapeutic radiation in a plane perpendicular to a direction of propagation of the therapeutic radiation. In particular, the radiation field describes an area that can be irradiated on the examination object or in a plane of the examination object. Herein, the radiation field is limited by the propagation of the therapeutic radiation. The propagation of the therapeutic radiation is described by a beam path. A projection of the beam path onto the plane of the examination object can describe the radiation field. Herein, the therapeutic radiation is emitted from a source. If the therapeutic radiation is X-radiation, the source is an X-ray source. The X-ray source can in particular be a linear accelerator.

The fin is formed to collimate therapeutic radiation. In particular, therapeutic radiation can be collimated with more than one fin. For this purpose, the fin is arranged between the examination object and the source. Collimation of the therapeutic radiation forms the radiation field with the fin such that tissue adjacent to the treatment area and/or organs positioned within the radiation field are shielded from the therapeutic radiation by the fin. In other words, an irradiated area on the examination object can be formed by arranging or positioning the fin in the beam path. In other words, the radiation field is restricted to the irradiated area by the at least one fin. In particular, the radiation field is restricted such that the area actually irradiated corresponds to the treatment area. This step is referred to as "collimation".

During collimation of therapeutic radiation by the fin, the intensity of the therapeutic radiation is attenuated on penetration of the fin such that the intensity of the therapeutic radiation behind the fin is negligibly low. IEC 60601-2-1

(2016) specifies standards for electron accelerators in the range of 1 MeV to 50 MeV. In particular, paragraph 201.10.1.2.103.2.1 a specifies that the intensity of X-radiation behind a fin should be at most 2% of the input intensity. In some embodiments of the present invention, the fin can be formed such that the intensity of X-radiation behind the fin is attenuated to at most 1% of the input intensity.

Herein, "behind" the fin refers to the view of the fin from the position of the source. Herein, the fin is arranged in such a way that the therapeutic radiation penetrates the fin at least in part of the collimation area. For this purpose, the collimation area of the fin is extended in the beam direction or direction of propagation of the therapeutic radiation. In particular, hereinafter, the extension of the fin in the beam direction is referred to as the "height" of the fin. In particular, the collimation area in the beam direction can have an extension of between 5 cm and 8 cm. In particular, the extension of the fin in the beam direction can be 5 cm, 5.5 cm, 6 cm, 6.5 cm, 7 cm, 7.5 cm or 8 cm. The collimation area of the fin is thus formed to be arranged at least partially in the beam path of the therapeutic radiation.

Perpendicular to the height and hence perpendicular to the beam path, the fin can have an extension of between 0.5 mm and 1 cm. In particular, the fin can have an extension of between 1 mm and 5 mm perpendicular to the height and perpendicular to the beam path. Hereinafter, this extension is referred to as the "thickness" of the fin. In particular, the fin can be between 2 mm and 3 mm thick.

The holding area is formed to be coupled to an adjustment device. Herein, the holding area and the collimation area are connected to one another, in particular soldered together. Adjusting the holding area with the adjustment device enables the collimation area to be adjusted or arranged or positioned in the beam path to restrict the radiation field.

Herein, the collimation area is made of the first material and the holding area is made of the second material. Herein, the first material and the second material are different from one another. Herein, the collimation area and the holding area are soldered together. In other words, the fin comprises a soldering point at which the collimation area and the holding area are connected to one another. In other words, the fin comprises a soldering point between the collimation area and the holding area. In other words, a contact surface of the holding area is connected or soldered to a contact surface of the collimation area at the soldering point.

The soldering point is in particular formed in such a way that a stable connection between the first and second material can be ensured. In particular, the soldering point is formed in such a way that no internal stress or stress occurs within the fin at the soldering point of the first and second material or that such stress is minimal. In particular, the soldering point is formed in such a way that heat input into the fin, for example by wire erosion, leads to no or only low (internal) stress between the first and second material at the soldering point. In particular, the soldering point is formed to compensate stresses caused by different coefficients of (thermal) expansion of the first and second material. Alternatively or additionally, the soldering point is formed as heat-resistant. In particular, the soldering point is formed in such a way that it can withstand short-term temperatures of more than 1000° C. during wire erosion. Alternatively or additionally, the soldering point is formed to withstand an application of force of up to 30 N/mm2 during milling or milling-out of the fin. In particular, the pressing point can be formed in such a way that it withstands an application of force of up to 50 N/mm2.

Herein, the first and/or second material meet at least one of the following criteria: radiation resistance (in particular up to approximately 250 kGy), operating temperature at least between 15 and 50° C., suitability for wire erosion (in particular resistivity of less than 100 Ωcm), hardness of at least 50 HV (in particular at least 70 HV, in particular at least 75 HV), machinability, high corrosion resistance. In particular, the first and/or second material can meet all these criteria.

The inventors have recognized that the use of different materials for the holding area and the collimation area enables the material costs of the fin to be minimized. In particular, the inventors have recognized that the requirements for the second material with respect to attenuation of therapeutic radiation are lower than they are for the first material. In particular, the inventors have recognized that thus a more cost-effective material can be selected for the holding area as the second material. The inventors have also recognized that the second material can be lighter than the first material. In this way, the weight of the fin can be reduced. This can in particular make the fin easier to handle. The inventors have recognized that the soldering enables a stress-free or low-stress connection to be formed at the soldering point, even if the first and second material have different coefficients of thermal expansion. The inventors have recognized that wire erosion for cutting out the fin after soldering is also possible. In other words, the soldering point is formed in such a way that no stresses, or only very low stresses, occur at the soldering point as a result of the wire erosion for cutting out the fin. The inventors have recognized that a fin formed in this way is in particular suitable for collimating therapeutic radiation in the form of X-radiation.

According to one or more example embodiments of the present invention, the first and second material are hard-soldered together.

Hard soldering is a soldering method performed at a temperature above 450° C. In particular, a solder that melts at a temperature of over 450° C. is used in hard soldering.

The inventors have recognized that the high temperatures in wire erosion can cause the soldering point to melt, in particular if a soft solder with a comparatively low melting point is used. The inventors have recognized that this can be prevented if the soldering point is established by hard soldering. The inventors have recognized that the high melting point of the hard solder prevents the soldering point from re-melting during wire erosion.

According to a one or more example embodiments of the present invention, the first and second material are paramagnetic.

In other words, the first and second material are not magnetizable. In particular, the magnetic permeability of the first and second material is less than 1.05 μ0. Herein, μ0 describes permeability in a vacuum. In other words, "paramagnetic" means that the first and second material have a permeability of less than 1.05 μ0.

The inventors have recognized that the use of paramagnetic materials also enables the fin to be used in a magnetic resonance tomography (MRT, also magnetic resonance imaging MRI) system. In particular, this enables radiotherapy to be given under MRT monitoring.

According to one or more example embodiments of the present invention, the first material is tungsten or a compound comprising tungsten.

Hereinafter, a compound comprising tungsten is also referred to as a tungsten compound. Herein, the tungsten compound advantageously comprises a tungsten content of at least 90%. In particular, the tungsten compound can comprise a tungsten content of at least 95%.

In particular, the tungsten compound can also comprise nickel. In particular, a copper-nickel compound can form a "binder" or a "matrix" in the tungsten compound. Alternatively, an iron-nickel compound can form the binder or the matrix if the fin does not have to be paramagnetic.

The inventors have recognized that tungsten is suitable for sufficiently attenuating, in particular collimating, therapeutic radiation, in particular X-radiation, in radiotherapy with a reasonable spatial extension, in particular reasonable height, of the collimation area. The inventors have recognized that, in order to collimate therapeutic radiation, at least the first material must be formed such that the therapeutic radiation is attenuated on penetration of the first material. The inventors have recognized that a binder made of copper-nickel can meet the paramagnetic requirements for the fin in an MRT.

According to one or more example embodiments of the present invention, the second material comprises titanium or stainless steel.

In particular, the second material can be more cost-effective than the first material. In particular, the second material is formed to be soldered to the first material. In other words, the second material is formed to be bonded with a solder that bonds to the first material. In particular, the second material can be machinable. In particular, the second material is corrosion-resistant. In particular, the second material can have a hardness of at least 50 HV, in particular at least 70 HV, in particular at least 75 HV.

In particular, the second material can alternatively or additionally comprise copper. In particular, the second material can be copper if the hardness requirements for the holder area are low.

In alternative embodiments of the present invention, the second material can comprise brass or bronze or an aluminum alloy. In particular, the first and second material can be soldered under a protective gas or in a vacuum.

The inventors have recognized that the second material does not have to meet any special requirements with regard to absorbency of therapeutic radiation, in particular X-radiation. The inventors have recognized that the use of a more cost-effective second material enables the fin to be manufactured in a more cost-effective way. The inventors have recognized that titanium and stainless steel meet the mechanical requirements for the second material. The inventors have recognized that it is easier to machine the second material than the first material, since the second material can in particular be less hard than the first material. The inventors have recognized that thus it is possible to accelerate and simplify a manufacturing process for the fin. The inventors have recognized that milling of the holding area made of the second material is simpler compared to a holding area made of the first material. The inventors have also recognized that the use of one of said materials as a second material can reduce the weight of the fin compared to a fin consisting entirely of tungsten or a tungsten compound. In this way, in particular handling can be improved.

According to one or more example embodiments of the present invention, the holding area and the collimation area are soldered with a copper solder or a god solder or a silver solder or a titanium solder.

In other words, the soldering point is formed with or by a copper solder or a gold solder or a silver solder or a titanium solder.

In particular, "copper solder" means that the solder used is copper-based. In other words, the largest component of a "copper solder" is copper. Analogously, the largest component of a "gold solder" is gold, that of a "silver solder" is silver and that of a "titanium solder" is titanium.

In particular, the solder can be a silver-copper solder (Ag—Cu) or a silver-copper-palladium solder (Ag—Cu—Pd) or a silver-copper-indium solder (Ag—Cu—In) or a silver-copper-indium-palladium solder (Ag—Cu—In—Pd). Herein, the elements are listed according to their content in the designation of the solder. For example, the component of silver is greater than the component of copper in the Ag—Cu solder.

In particular, the soldering point between the holding region and the collimation area can be formed with a solder containing Ag59Cu27.25In12.5Ti1.25.

In particular, the solder for soldering the holding area and the collimation area can be an active solder. In particular, a small proportion of titanium is added to one of the aforementioned solders for this purpose. In particular, the titanium content may comprise up to 5 percent by mass. In particular, this can improve the stability of the soldering point.

Alternatively, aluminum and/or vanadium or a combination of titanium and aluminum may be added to an active solder instead of titanium.

In particular, the solder used has the lowest possible melting point in the range of hard solders.

The inventors have recognized that said solders can form a stable bond with the first and second material. The inventors have recognized that the melting point of said solders is high enough to ensure that the soldering point does not melt due to the short temperature input during wire erosion. The inventors have recognized that the melting point of said solders is as low as possible to minimize the temperature input or heat input into the first and second material during soldering. The inventors have recognized that in this way stresses or internal stresses between the first and second materials can be reduced or prevented by soldering. The inventors have recognized that in particular Ag59Cu27.25In12.5Ti1.25 solder has advantageous properties (low melting point for a hard solder, good adhesion to the first and second material).

According to one or more example embodiments of the present invention, a compensating layer is arranged between the first material and the second material. The compensating layer is formed from a compensating material that compensates a difference between the coefficients of thermal expansion of the first material and the second material.

In particular, the compensating layer is arranged at the soldering point. In particular, the compensating layer can form the soldering point. In particular, the compensating layer can be formed from the solder used to solder the first and second material. Alternatively, the compensating layer can be formed from a material that can be arranged between the first and second material during soldering of the first and second material.

In particular, the compensating layer can comprise copper.

In particular, the compensating layer can be between 0.25 mm and 1 mm thick. In particular, the compensating layer can be approximately 0.5 mm thick.

The inventors have recognized that the compensating layer can compensate for possible stresses between the first and second material, in particular due to a difference between the coefficients of thermal expansion of the first and second material. Such stresses or internal stresses can occur in particular due to heat input. Heat input can occur in particular due to soldering of the first material and the second material and/or wire erosion and/or absorption of therapeutic radiation.

The inventors have recognized that the compensating layer can compensate for possible stresses between the first and second material, in particular due to a difference between the coefficients of thermal expansion of the first and second material. Such stresses or internal stresses can occur in particular due to heat input. Heat input can occur in particular due to soldering of the first material and the second material and/or wire erosion and/or absorption of therapeutic radiation.

According to another aspect of the invention, the compensating layer can be formed by a copper plate.

The copper plate can in particular have a thickness of between 0.25 mm and 1 mm. In particular, the copper plate can be 0.5 mm thick. The copper plate is arranged between the holding area and the collimation area. In particular, the copper plate is arranged in the soldering point. The copper plate is soldered to the holding area and the collimation area. In other words, the holding region and the collimation area are soldered to each other via the copper plate. The copper plate can be soldered to the first material with a first solder and to the second material with a second solder. Herein, the first solder and the second solder may be the same or different. In particular, herein, the first solder and the second solder can each be one of the aforementioned solders. In particular, the solder with which the copper plate is soldered to the first or the second material has a lower melting point than copper. In particular, the melting point of the solder is thus lower than 1084° C. In particular, the copper plate can be soldered to the first and/or second material using the Ag59Cu27.25In12.5Ti1.25 solder.

The extension of the copper plate corresponds to the extension of the contact surfaces of the holding area and the collimation area. In other words, the copper plate in the soldering point covers the contact surfaces of the holding area and the collimation area.

The inventors have recognized that copper can compensate a difference between the coefficients of thermal expansion of the first material and second material. The inventors have recognized that copper can be stably soldered to the first material and the second material. The inventors have recognized that inserting a copper plate as a compensating layer, as opposed to a copper solder as a compensating layer, has the advantage that a solder with a lower melting point than a copper solder can be used. In this way, stresses due to heat input by soldering between the holding area and the collimation area can be reduced or prevented.

According to one or more example embodiments of the present invention, the compensating layer can be formed by a plate made of a third material, wherein a coefficient of thermal expansion of the third material lies between the coefficient of thermal expansion of the first material and the coefficient of thermal expansion of the second material.

In particular, the compensating layer can be formed by a titanium plate. In other words, the third material can be titanium. The titanium plate can be formed as described above with respect to the copper plate.

The inventors have recognized that by a third material formed in this way, a transition can be formed between the coefficient of thermal expansion of the first material and the coefficient of thermal expansion of the second material by the third material.

According to one or more example embodiments of the present invention, the compensating layer is formed by a net-like element and a solder. Herein, the net-like material is in particular made of nickel.

The solder can in particular be one of the solders mentioned above. In particular, the solder can be a copper solder.

The net-like element is in particular formed to "soak up" the solder. In particular, the net-like element can "become saturated" with the solder during soldering. In other words, the net-like element is spongy. In some embodiments, the net-like element can be ductile.

The net-like element can in particular be made of nickel. In other words, the net-like element can be a nickel net.

The net-like element forms the compensating layer between the holding area and the collimation area after it has been saturated with the solder. In other words, the holding area is soldered to the collimation area via the net-like element. In other words, the net-like element and the solder form the soldering point. Herein, the net-like element extends over the contact surfaces of the holding area and the collimation area.

The inventors have recognized that a sufficient layer thickness of the compensating layer can be achieved by the solder being "held" or "bound" in the net-like element. In other words, the net-like element prevents the solder from running away during soldering and only a very thin compensating layer being able to be formed. The inventors have recognized that the nickel net has a higher melting point than the aforementioned solders, in particular the copper solders. The inventors have recognized that the compensating layer formed in this way is formed to compensate or reduce or prevent stresses or internal stresses between the first and the second material. The inventors have recognized that a copper solder is in particular suitable for compensating for such stresses.

According to one or more example embodiments of the present invention, the fin comprises a guide element. Herein, the guide element is formed by the first and second material.

The guide element is in particular arranged on the side of the fin facing the radiation source. Alternatively or additionally, a further guide element can be arranged on the side of the fine facing away from the radiation source. The guide element is formed to stabilize the fin during adjustment with the adjustment device. In particular, the guide element prevents the fin from twisting or tilting relative to the beam direction. In particular, the fin is adjusted or moved further into the radiation field or beam path or further out of the radiation field or beam path along the guide element during adjustment of the collimation area.

In particular, the guide element can be formed to be guided in a guide system. Herein, the guide system comprises a counterpart to the guide element. The guide system can be stationary relative to the source of the therapeutic radiation.

In particular, the guide element can be formed as a guide rail or as a guide strip.

The guide element extends at least partially over the collimation area and at least partially over the holding area. In particular, the guide element is thus formed from the first and second material. In particular, the guide element can be formed by milling. The inventors have recognized that the fin can be stabilized by the guide element during adjustment by the adjustment device. The inventors have also recognized that the guide element can be milled in after the soldering. In this way, it can be ensured that the guide element does not warp as the result of a method step carried out later during the manufacture of the fin. The inventors have recognized that in this way the guide element can be formed over the soldering point.

One or more example embodiments of the present invention also relates to a collimator. The collimator comprises a plurality of fins as described above and an adjustment device. Herein, the fins are coupled with their holding areas to the adjustment device. Herein, the adjustment device is formed to adjust each fin of the plurality of fins perpendicular to a contact surface of the holding area and the collimation area.

The plurality of fins comprise at least two fins formed according to one of the above-described aspects. The plurality of fins are arranged next to one another in the collimator. In other words, the fins are arranged side surface to side surface. Herein, each of the fins is coupled to the adjustment device via its holding area. In particular, each fin can be adjusted in a plane parallel to its side surface with the adjustment device. In particular, each fin can be adjusted perpendicular to the contact surfaces of the holding area and the collimation area or perpendicular to the soldering point with the adjustment device.

A side surface of the fin is defined by the height of the fin and formed by the first and second material. In other words, the side surface extends over the holding area and the collimation area. Herein, a fin comprises two side surfaces. Herein, the two side surfaces of a fin are spaced apart by a distance corresponding to the thickness of the fin.

According to one or more example embodiments of the present invention, the collimator can comprise a guide system as described above. In particular, the guide system can be formed to guide the fins along their at least one guide element. In particular, the guide system is formed to prevent lateral tilting of the fins. In other words, the guide system stabilizes an alignment of the fins.

The inventors have recognized that a plurality of fins can be arranged in a collimator. The inventors have recognized that the radiation field can be restricted to the treatment area by adjusting the fins with the adjustment device. The inventors have recognized that the holding area does not have to be arranged in the beam path for this purpose. The inventors have recognized that for this reason the second material does not have to meet the requirement with regard to the attenuation of the therapeutic radiation. The inventors have recognized that the holding area only forms a mechanical coupling of the collimation area with the adjustment device.

One or more example embodiments of the present invention also relates to a method for manufacturing a fin as described above. The method comprises a method step of soldering together a first block made of the first material and a second block made of the second material to form a combination block.

The first and the second block are in particular cuboidal or crescent-shaped. During the soldering together of the first and second block, the soldering point is formed between the two blocks. Thus, the soldering point is formed by an at least approximately rectangular contact surface of the first block and an at least approximately rectangular contact surface of the second block. Herein, the combination block comprises the first and second block connected via the soldering point.

The first block and the second block have at least one thickness corresponding to the thickness of the fin. In other words, the first and second block are at least 0.5 mm to 10 mm, in particular at least 1 mm to 5 mm, thick. In particular, the first and second block can have a thickness of between 2 mm and 3 mm. The thickness of the blocks describes an extension parallel to the contact surfaces. The contact surfaces are thus extended at least 0.5 mm to 10 mm, in particular at least 1 mm to 5 mm, in one direction. In some embodiments, the contact surfaces can be extended at least 2 mm to 3 mm in one direction.

In particular, the at least approximately rectangular contact surfaces can be extended between 2 mm and 40 mm in one direction. In particular, the at least approximately rectangular contact surfaces can be extended between 20 mm and 80 mm in the direction perpendicular thereto. In particular, the contact surfaces of the first and second block can each comprise an area of approximately 64 mm×25 mm.

In particular, the first block can have an extension of between 100 mm and 180 mm in the direction perpendicular to the contact surface. In particular, the extension of the first block perpendicular to the contact surface can be approximately 140 mm.

In particular, the second block can have an extension of between 150 mm and 300 mm in the direction perpendicular to the contact surface. In particular, the extension of the second block perpendicular to the contact surface can be approximately 230 mm.

The inventors have recognized that the soldering or forming of the soldering point takes place before the precise shaping of the fin based on two blocks. The inventors have recognized that the effect of heat from the soldering would deform an already precisely formed fin in such a way that the accuracy requirements would no longer be met. The inventors have recognized that this problem can be solved by soldering together the first and second material before the fin is shaped. The inventors have recognized that deformation during the soldering together of the blocks can still be compensated subsequently when the fin is shaped or cut out. The inventors have also recognized that cuboidal or crescent-shaped blocks are easy to handle during soldering.

According to one or more example embodiments of the present invention, the method step of soldering comprises a method step of applying a solder and a method step of joining together the first and second block.

In particular, in the method step of applying the solder, the solder is applied to the contact surfaces of the first and/or second block. The solder can be solid at room temperature. The solder can be placed on the contact surfaces at room temperature. For this purpose, the solder can be shaped in the form, a plate, for example.

In the method step of joining together the first and second block, the soldering point is formed after the solder has been applied. In particular, the first and second block are joined together to form the combination block. In particular, the first and second block are joined together at their contact surfaces. In particular, the first and second block can be joined together under protective gas or under a vacuum (<10-5 mbar). In particular, the first and second block can be joined together at a temperature which corresponds to a melting point of the solder or is slightly above this temperature. In this way, the solder fuses with the first and second blocks when they are joined together. The solder can in particular be one of the aforementioned solders.

In some embodiments of the present invention, the compensating layer can be introduced between the first and second block before the first and second block are joined together. In particular, in some embodiments of the present invention, the first and second block can be joined together via the compensating layer.

In particular, the solder can then be applied between the compensating layer and the contact surface of the first block and between the compensating layer and the contact surface of the second block in the method step of applying the solder. If the solder is in the form of a plate, a soldercompensating-layer-solder layer can be introduced or applied between the contact surfaces.

According to one or more example embodiments of the present invention, the method step of soldering comprises a method step of cooling down the combination block.

In particular, in the method step of cooling down the combination block, the combination block is cooled along a planned or fixed temperature curve after it has been assembled. In particular, the cooling down or cooling takes place in such a way that the first and the second material and a material of the compensating layer and the solder are not magnetized. In addition, the cooling down or cooling takes place in such a way that, if possible, no stresses occur in the combination block due to excessively rapid cooling down or cooling.

The inventors have recognized that selective cooling down can enable stresses or internal stresses in the combination block, and thus in the fin, to be avoided or reduced. The inventors have also recognized that unwanted magnetization of the combination block can be prevented by selective cooling down.

According to one or more example embodiments of the present invention, the method step of soldering comprises a method step of cleaning the contact surfaces of the first and second block.

In particular, the contact surfaces can be cleaned mechanically and/or wet-chemically. Alternatively or additionally, the contact surfaces can be cleaned using plasma cleaning. In particular, the contact surfaces are cleaned before the method step of applying the solder.

In particular, a flux can additionally be applied to the contact surfaces before the solder is applied if a time interval between cleaning and applying the solder is too long.

The inventors have recognized that the solder binds better with the cleaned contact surface. In other words, a more stable soldering point can be formed by cleaning. The inventors have found that the flux prevents the contact surfaces from being recontaminated. Alternatively, the flux can clean the contact surfaces again due to the temperature input during soldering or when applying the solder and when joining the blocks together.

According to one or more example embodiments of the present invention, the soldering method step can comprise a method step of annealing the first and/or second block.

In particular, the first and second block can be heated to approx. 800° C. In particular, the first and second block can be annealed at about 800° C. for at least 150 minutes. In particular, the first and second block can be positioned in a vacuum (<10-5 mbar) during annealing.

The annealing in particular takes place before the solder is applied. Annealing can take place before or after cleaning of the contact surfaces.

The inventors have recognized that annealing reduces stresses or internal stresses that are already present in the first and/or second block before the first and second block are joined together.

According to one or more example embodiments of the present invention, the method also comprises a method step of cutting out the fin from the combination block by wire erosion.

In particular, the fin is cut off or cut out from the combination block as a "slice". In particular, the "slice" is arranged in the combination block perpendicular to the soldering point. In particular, the side surfaces of the fin can be shaped during the cutting out. Herein, as described above, the side surfaces are the two surfaces of the fin which are formed by the first and second material and extend over the height of the fin. The side surfaces of the fin are aligned parallel to the beam direction during collimation of the therapeutic radiation.

In particular, a thickness of the fin can be formed variably along the height. In particular, hence, this allows cone beam geometry to be taken into account during the propagation of the therapeutic radiation. In particular, this variable thickness can be shaped when the fin is cut out by the shaping of the side surfaces. In particular, the shaping of the side surfaces enables the fin to be shaped in such a way that a cross-sectional area of a cross section through the collimation area parallel to the soldering point corresponds to a cross-sectional area of a truncated cone or a trapezoid. In particular, the thickness of the fin is then defined by a maximum and a minimum thickness.

In particular, more than one fin can be cut out of or cut off the combination block. In particular, two or more fins can be cut off the combination block in slices. Herein, in each case "a waste slice" can be cut off the combination block between the fins. In this way, the side surface of each fin can be formed or shaped by wire erosion.

The inventors have recognized that wire erosion enables the required accuracy to be achieved when the fin is cut out. The inventors have recognized that soldering together the first and second material before cutting out prevents the fin from being deformed by a subsequent heat effect due to the joining or soldering together of the holding area and the collimation area. The inventors have recognized that a soldering point formed as described above is able to absorb any possible stresses caused by the temperature input between the two blocks or between the first and second material during wire erosion. The soldering point ensures a stable connection between the first and second material even during or after wire erosion. The inventors have recognized that the soldering point established by hard soldering is sufficiently temperature-resistant not to melt during wire erosion.

According to one or more example embodiments of the present invention, the method also comprises a method step of milling out at least one side surface of the fin out from the combination block.

Herein, the side surface is formed as described above.

In particular, with this manufacturing method, the thickness of the combination block is equal to or only slightly greater than the thickness of the fin. The thickness of the combination block is dictated by the thickness of the first or second block. In particular, the thickness of the combination block can be equal to or 5% or 10% greater than the thickness of the fin.

In particular, the form of the side surfaces can be formed or shaped during milling. In particular, the shaping of the side surfaces can create a variable thickness of the fin over the height of the fin.

The inventors have recognized that the soldering point remains stable even when force is applied due to milling. In other words, the inventors have recognized that the soldering point also withstands the application of force due to milling.

According to one or more example embodiments of the present invention, the method step of soldering comprises a method step of introducing a compensating layer between the contact surfaces to be soldered of the first and second block.

In particular, the compensating layer is formed as described above. In particular, the compensating layer can be formed by a copper plate or by a net-like element in combination with the solder.

The compensating layer is in particular introduced between the blocks before the first and second blocks are joined together. In particular, when the first and second blocks are joined together, the compensating layer is soldered to the contact surface of the first block. In particular, when the first and second blocks are joined together, the compensating layer is also soldered to the contact surface of the second block. The first and the second block are thus joined together via the compensating layer.

The inventors have recognized that the compensating layer can easily be introduced between the two blocks in the soldering method step. In particular, the subsequent cutting out or milling out of the fin or the side surface of the fin can prevent stresses from being introduced into the fin at the soldering point by wire erosion and/or milling.

According to one or more example embodiments of the present invention, the method also comprises the method steps of milling out at least one guide element from the combination block and/or milling out a contour of the holding area from the combination block.

Herein, the guide strip is formed as described above. Herein, the guide strip can be milled out before the fin is cut out from the combination block. Alternatively, the guide strip can be milled out after the fin is cut out from the combination block.

The contour of the holding area describes a manifestation of the edges of the holding area that is not in contact with the collimation area. In particular, the contour describes a contour of the side surface of the fin in the holding area.

In particular, the contour is formed in such a way that the holding area can be coupled to the adjustment device. In particular, the contour of the holding area can form a bar with which the holding area can be coupled to the adjustment device.

In particular, the contour can be formed in such a way that the holding area is as weight-saving as possible. In particular, the holding area can comprise at least one cut-out in the area of the side surface of the fin formed by the holding area. In other words, the contour can comprise at least one cut-out.

In particular, the method step of milling out the contour of the holding area can be executed before the fin or the side surface of the fin is cut or milled out from the combination block. Alternatively, the method step of the milling-out of the contour of the holding area can take place after the fin or the side surface of the fin is cut or milled out from the combination block. Alternatively, the contour of the holding area can take place partially before and partially after the fin is cut out from the combination block.

The inventors have recognized that milling out the guide element and/or the contour of the holding area before the fin is cut out from the combination block can prevent warping or deformation of the fin.

FIG. 1 shows a first exemplary embodiment of a fin 1 for collimating therapeutic radiation.

The fin 1 comprises a holding area 12 and a collimation area 11. The holding area 12 and the collimation area 11 are connected to one another via a soldering point 13. In other words, the holding area 12 and the collimation area 11 are soldered together.

Figure 2:
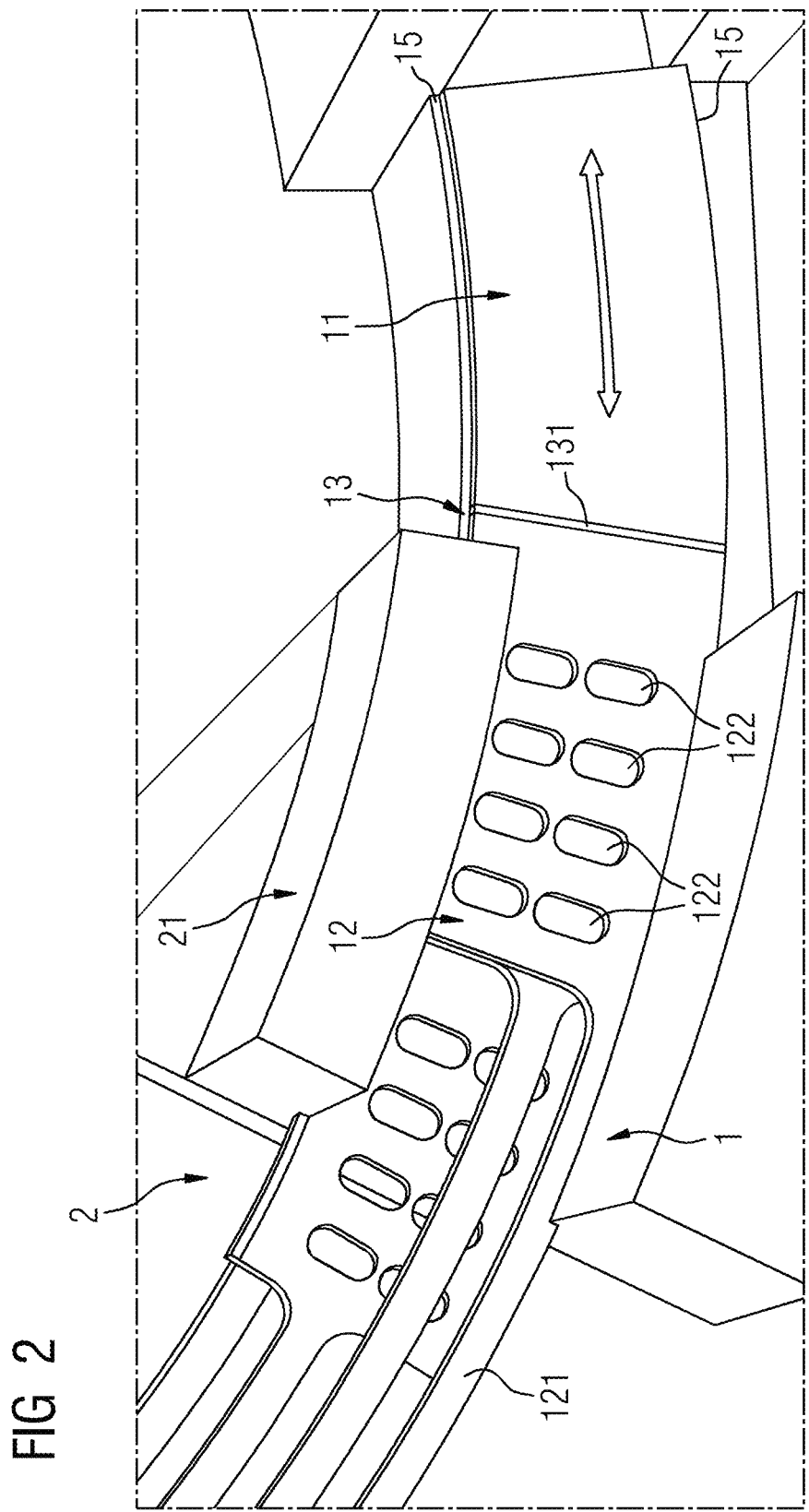

The fin 1 can in be arranged in a therapeutic radiation beam path for radiotherapy. Herein, in an advantageous embodiment of the present invention, the therapeutic radiation can be X-radiation. In alternative embodiments, the therapeutic radiation can be particle radiation. Herein, the beam path describes the propagation of the therapeutic radiation. The beam path delimits a radiation field. Herein, the radiation field describes an area in a plane in which the therapeutic radiation propagates or onto which the therapeutic radiation is irradiated. In radiotherapy, a treatment area of an examination object is irradiated with therapeutic radiation. Radiotherapy with X-radiation as therapeutic radiation typically uses ultra-hard X-radiation (>1 MeV). In particular, X-radiation with energy greater than or equal to 6 MeV can be used. In order to ensure that only the treatment area is irradiated with the therapeutic radiation, the radiation field is restricted by collimation of therapeutic radiation with at least one fin 1. In particular, herein, the fin 1 can be arranged in a collimator 2 as part of a plurality of fins 1, as depicted in FIG. 2. In the depicted alignment of the fin 1, a source of the therapeutic radiation, in particular an X-ray source, is arranged above the fin 1. The examination object is arranged below the fin 1. The therapeutic radiation penetrates the fin 1 parallel to its height. In the depicted alignment, the therapeutic radiation penetrates the fin 1 from top to bottom. FIG. 1 shows a top view of a side surface of the fin 1. Herein, a thickness of the fin 1 describes an extension of the fin 1 into the image plane. The fin 1 can have a thickness of between 0.5 mm and 10 mm. In particular, the fin 1 can have a thickness of between 1 mm and 5 mm. In particular, the fin 1 can have a thickness of between 2 mm and 3 mm. In particular, the thickness of the fin 1 can vary over the height. In particular, the fin 1 can be thinner at a top edge of the side surface than at a bottom edge. Herein, "top" and "bottom" refer to the depiction according to FIG. 1. In other words, a cross section perpendicular to the image plane through the fin 1 can be a cross section of a truncated cone or a trapezoid. In particular, the thickness of the fin 1 is then defined by a maximum and a minimum thickness.

The collimation area 11 is made of a first material. Herein, the first material is formed to collimate therapeutic radiation, in particular X-radiation. In other words, the first material is formed to attenuate the intensity of the therapeutic radiation in such a way that the intensity of the therapeutic radiation is negligible after penetrating the collimation area 11. In particular, if the therapeutic radiation is X-radiation, the intensity of the X-radiation can be attenuated to at most 2% of the incident intensity by the penetration of the fin 1. In some embodiments of the present invention, the intensity of the X-radiation can be attenuated to at most 1% of the incident intensity by the penetration of the fin 1.

In some embodiments of the present invention, the first material can in particular be tungsten or a compound comprising tungsten or tungsten compound. Herein, the compound comprising tungsten comprises a tungsten content of at least 90%. Herein, the compound comprising tungsten in particular comprises a tungsten content of at least 95%. The compound comprising tungsten also comprises a binder or a matrix. The binder can in particular be iron-nickel or copper-nickel.

The holding area 12 is formed so it can be coupled to an adjustment device. In particular, the holding area 12 can be coupled to the adjustment device by a bar 121. Herein, the bar 121 can be formed at any height of the fin 1. In particular, in the case of different fins 1 in a collimator 2 according to FIG. 2, the bar 121 can be formed at different heights to enable easy or simple adjustment. In particular, in this way, this can prevent the fins 1 in the collimator 2 interfering with each other during adjustment with the adjustment device. The holding area 12 can comprise at least one cut-out 122. The cut-out 122 can reduce the weight of the holding area 12. In particular, the weight can be reduced without impairing the stability of the holding area 12. In particular, a contour of the holding area 12 can be defined by the bar 121 and/or the at least one cut-out 122. The holding area 12 is made of a second material. In some embodiments of the present invention, the second material can in particular comprise stainless steel or titanium. In alternative embodiments, the second material can comprise brass or bronze or an aluminum alloy.

In some embodiments of the present invention, the first and second material can be paramagnetic. In particular, the magnetic permeability of the first and second material is then less than 1.05 μ0. In particular, the binder of the collimation area 11 can then be copper-nickel.

In some embodiments of the present invention, the first and/or second material can meet at least one of the following criteria: radiation resistance (in particular to approximately 250 kGy), operating temperature at least between 15 and 50° C., suitability for wire erosion (in particular resistivity of less than 100 Ωcm), hardness of at least 50 HV (in particular at least 70 HV or 75 HV), machinability, high corrosion resistance. In particular, the first and/or second material can meet all these criteria.

The collimation area 11 and the holding area 12 or the first and second material are soldered together or connected to one another. In particular, a contact surface of the collimation area 11 is pressed together with a contact surface of the holding area 12. In particular, the collimation area 11 and the holding area 12 are soldered together at the soldering point 13.

In some embodiments of the present invention, the collimation area 11 and the holding area 12 are connected or soldered to one another.

The solder for soldering the collimation area 11 and the holding area 12, in particular the hard solder, can be a copper solder, a gold solder, a silver solder or a titanium solder. In other words, the soldering point 13 can be formed by a copper solder, a gold solder, a silver solder or a titanium solder. In this case, copper has the greatest material content in a copper solder. Analogously, gold or silver or titanium have the greatest material content in a gold solder or silver solder or titanium solder, respectively.

In particular, the solder may be one of the following silver solders: silver-copper solder or silver-copper-palladium solder or silver-copper-indium solder or a silver-copper-indium-palladium solder.

In particular, the solder may be an Ag59Cu27.25In12.5Ti1.25 solder.

In particular, the solder can be an active solder. One of the aforementioned solders can be mixed with a small content of titanium. The titanium content is a maximum of 5 percent by mass. The stability of the soldering point 13 is improved by the content of titanium.

Alternatively, instead of the titanium, a small content of aluminum and/or vanadium or a combination of titanium and aluminum can be added to the active solder.

In some embodiments of the present invention, a compensating layer 131 can be arranged between the contact surfaces of the holding area 12 and the collimation area 11. In particular, the collimation area 11 and the holding area 12 are then soldered to one another via the compensating layer 131. In particular, the soldering point 13 is formed by the solder and the compensating layer 131. In particular, the contact surface of the collimation area 11 is soldered to one side of the compensating layer 131 and the contact surface of the holding area 11 is soldered to the other side of the compensating layer 131. Herein, the compensating layer 131 fills a complete gap between the collimation area 12 and the holding area 11. Herein, the compensating layer 131 has a thickness of between 0.25 mm and 1 mm, in particular 0.5 mm. In other words, the compensating layer 131 fills a gap between the collimation area 11 and the holding area 12 with a gap width of between 0.25 mm and 1 mm, in particular 0.5 mm.

The compensating layer 131 is formed by a compensating material. The compensating layer 131 can in particular be formed by a ductile material. The compensating material is formed to compensate a difference in the coefficients of thermal expansion of the first and the second material.

In some embodiments of the present invention, the compensating layer 131 can be formed by a copper plate. In particular, the copper plate is soldered to the contact surface of the holder area 12 and to the contact surface of the collimation area 11. In particular, the solder used to solder the copper plate has a lower melting point than copper, i.e., a melting point below 1084° C.

Alternatively, the compensating layer 131 can be formed from a third material other than copper with a coefficient of thermal expansion between the coefficient of thermal expansion of the first material and the coefficient of thermal expansion of the second material. In particular, the third material can be titanium. Then the compensating layer 131 can be formed by a titanium plate.

In alternative embodiments of the present invention, the compensating layer 131 can be formed by a net-like element in combination with the solder. The net-like element prevents the solder from "running away" or "running off" during the soldering process. The net-like element soaks up the solder during soldering. The net-like element endows the solder with the stability to form the compensating layer in the desired thickness. The net-like element is formed in a spongy manner. The net-like element can in particular be a nickel net.

In some embodiments of the present invention, the fin 1 can comprise at least one guide element 15. The guide element 15 can be arranged at the top edge or at the bottom edge of the fin 1 or the side surface of the fin 1. In particular, one guide element 15 can be arranged at the top edge and one guide element 15 at the bottom edge of the side surface. The at least one guide element 15 can be a guide strip or a guide rail. The guide element 15 is formed to prevent tilting of the fin 1 during adjustment of the fin 1 with the adjustment device. In particular, the fin 1 can be adjusted along the at least one guide element 15. Herein, the guide element 15 is formed by the first and second material. In other words, the at least one guide element 15 extends at least partially over the holding area 12 and at least partially over the collimation area 11. In particular, the at least one guide element 15 can be milled into the first and second material. In other words, the guide element 15 can be milled out of the first and the second material.

FIG. 2 shows an exemplary embodiment of a collimator 2.

The collimator 2 comprises a plurality of fins 1. In the exemplary embodiment depicted, the collimator 2 comprises fins 1 formed according to the exemplary embodiment depicted in FIG. 1. Alternatively, the collimator 1 can also comprise other embodiments of the fin 1 according to the present invention. Each of the fins 1 is coupled by a bar 121 to an adjustment device. Herein, the fins 1 can be adjusted according to the direction depicted by the double arrow. Herein, the bars 121 of the different fins 1 are arranged at different heights on the corresponding fin 1. In particular, the adjustment of the fins 1 can be simplified in this way. In particular, in this way, this can prevent the fins 1 interfering with each other during adjustment.

The collimator 2 also comprises a guide system 21. The fins 1 can be stabilized with the guide system 21 during adjustment. In particular, herein, the fins 1 are guided along their guide elements 15 in the guide system 21. In particular, lateral tilting of the fins can be prevented in this way.

Figure 3:
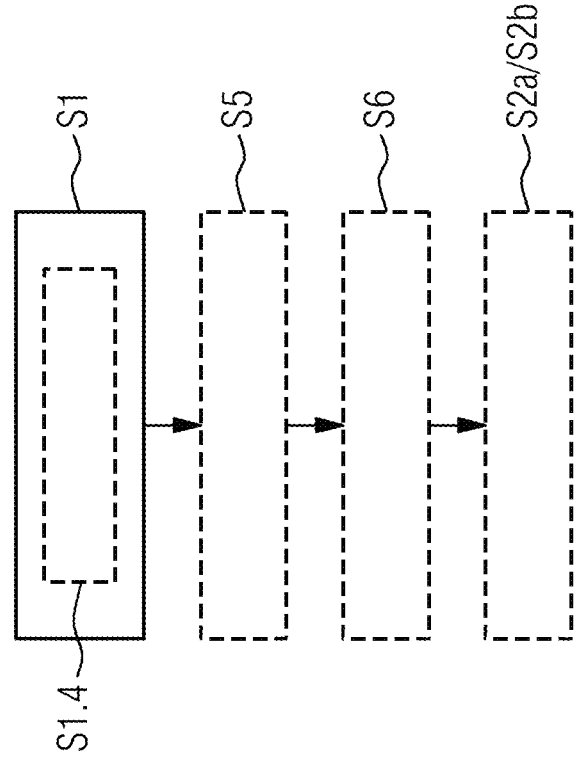

FIG. 3 shows a first exemplary embodiment of a method for manufacturing a fin 1 for collimating therapeutic radiation.

In particular, this depicts a method for manufacturing a fin 1 according to the exemplary embodiment depicted in FIG. 1.

The method steps depicted in dashed lines are optional method steps which may be comprised by the method in dependence on the properties of the fin 1 manufactured.

The method comprises a method step of a soldering together S1 a first block made of the first material and a second block made of the second material. Herein, the blocks are soldered together or connected to one another to form a combination block.

During the soldering S1, the soldering point 13 is formed between the first and second block. Herein, the first and second block are in particular cuboidal or crescent-shaped. Herein, each of the blocks has a thickness corresponding at least to the (maximum) thickness of the fin 1.

During the soldering S1, in each case a contact surface of the first block is soldered to a contact surface of the second block. Herein, the contact surfaces can be formed as rectangular. In particular, the rectangular contact surfaces can be extended between 2 mm and 40 mm in one direction. In particular, the rectangular contact surfaces can be extended between 20 mm and 80 mm in the direction perpendicular thereto. In particular, the contact surfaces can in each case comprise an area of approximately 64 mm×25 mm.

In particular, the first block can have an extension of between 100 mm and 180 mm in the direction perpendicular to the contact surface. In particular, the extension of the first block perpendicular to the contact surface can be approximately 140 mm.

In particular, the second block can have an extension of between 150 mm and 300 mm in the direction perpendicular to the contact surface. In particular, the extension of the second block perpendicular to the contact surface can be approximately 230 mm.

In particular, the first and second blocks can be soldered together via a compensating layer 131. In other words, the contact surface of the first block can be soldered to the compensating layer 131 and the contact surface of the second block can be soldered to the compensating layer 131.

In this case, the method step of soldering S1 can comprise an optional method step of introducing S1.4 the compensating layer 131. In particular, the compensating layer 131 is arranged between the first and the second block, in particular between the contact surfaces of the blocks. The compensating layer 131 is formed as described in FIG. 1.

The method comprises an optional method step of cutting out S2a the fin 1 from the combination block by wire erosion.

In particular, the side surfaces of the fin 1 are shaped or cutout during the cutting-out S2a of the fin 1 from the combination block by wire erosion.

In some embodiments of the present invention, more than one fin 1 can be cut out from the combination block in the method step of cutting out S2a.

Alternatively to the method step of cutting out S2a the fin 1 by wire erosion, the method can optionally comprise a method step of milling out S2b at least one side surface of the fin 1 from the combination block.

In particular, in the method step, both side surfaces of the fin 1 can be milled out from the combination block. In other words, the side surface of the fin 1 can be shaped during milling-out S2b of the side surface. In particular, the wording "the side surface is milled out from the combination block" is synonymous with the wording "the fin 1 is milled out from the combination block". In particular, the thickness of the combination block corresponds to the (maximum) thickness of the fin 1. Alternatively, the combination block is only slightly, in particular at most 10%, thicker than the fin.

In an optional method step of milling out S5 at least one guide element 15, the at least one guide element 15 can be milled out before the cutting-out S2a or milling-out S2b of the fin 1 from the combination block. In particular, the at least one guide element 15 is milled out parallel to the side surface of the fin 1. Herein, the at least one guide element 15 is formed as in the description of FIGS. 1 and 4.

Alternatively, the method step of milling out S5 the at least one guide element 15 can be executed after the optional method step of milling out S2b at least one side surface of the fin 1.

The method also comprises an optional method step of milling out S6 a contour of the holding area 12 from the combination block.

In particular, herein, the bar 121 and the at least one cut-out 122 of the holding area 12 are milled out. Thus, in particular, the contour of the holding area 12 in the area of the combination block is formed by the second material. The method step of milling out S6 the contour of the holding area 12 can be executed before or after the milling-out S5 of the at least one guide element 15.

In particular, the method step of milling out S6 the contour of the holding area 12 can be executed before cutting out S2a the fin or milling out S2b the at least one side surface of the fin 1. Alternatively, the contour of the holding area 12 can be milled out of the fin 1 that has already been cut off or milled out. In other words, the method step of milling out S6 the contour of the holding area 12 can be executed after the method step of cutting out S2a the fin or milling out S2b the at least one side surface of the fin 1. Alternatively, the method step of milling out S6 the contour of the holding area 12 can be executed partially before and partially after the method step of cutting out S2a the fin or of milling out S2b the at least one side surface of the fin 1. For example, the bar 121 can be milled out beforehand and the at least one cut out 122 afterward.

Figure 4:
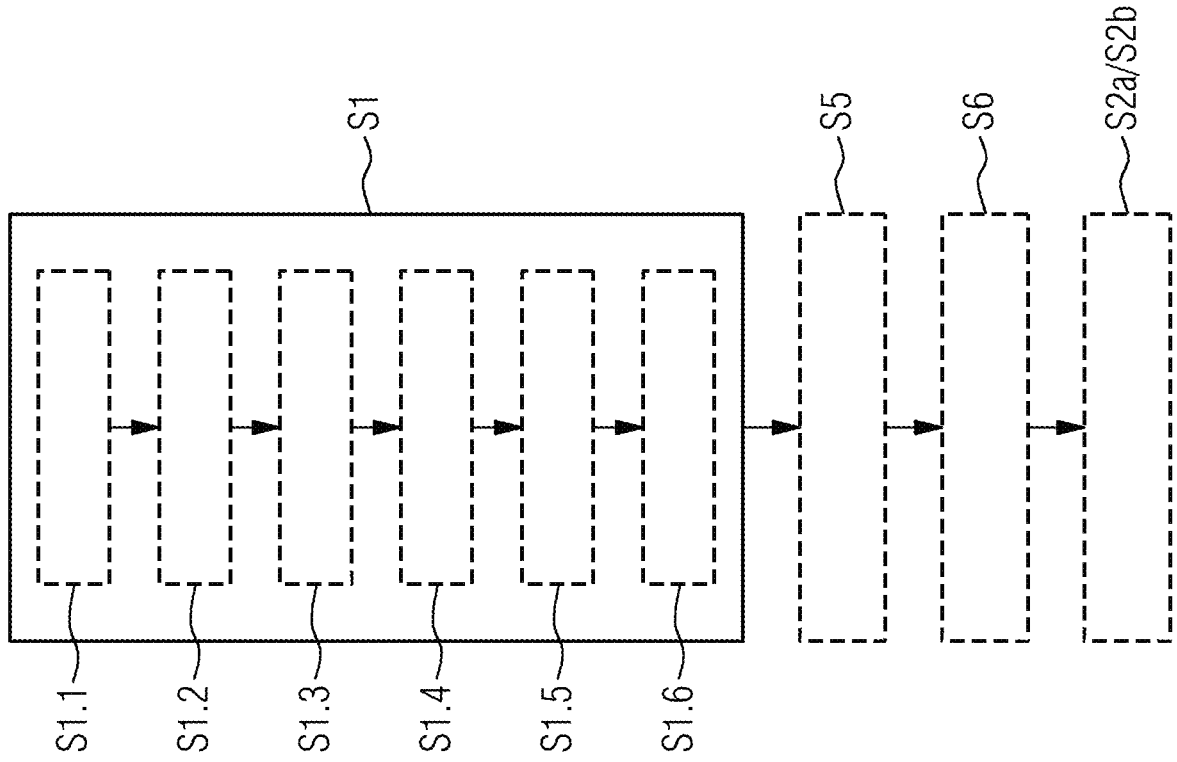

FIG. 4 shows a second embodiment of a method for manufacturing a fin 1 for collimating therapeutic radiation.

The method steps already described in the description of FIG. 3 are formed analogously.

The method step of soldering S1 comprises an optional method step of cleaning S1.1 the contact surfaces. In the method step of cleaning S1.1 the contact surfaces, the contact surfaces of the first and the second block are cleaned.

Herein, the contact surfaces are cleaned in such a way that a better connection between the contact surfaces and the solder can be established. In particular, the contact surfaces can be cleaned of oxides. In particular, the contact surfaces can be cleaned mechanically and/or wet-chemically. Alternatively or additionally, the contact surfaces can be cleaned by plasma cleaning.

In particular, a flux can be applied to the contact surfaces after cleaning if a time period until the next method step may be too long. In this way, oxides or similar can be prevented from forming again on the contact surfaces, or these are removed from the surface again by heating the flux.

The method step of soldering S1 comprises an optional method step of annealing S1.2 the first and/or second block.

In particular, the method step of annealing S1.2 can be performed before or after the cleaning S1.1 of the contact surfaces.

During the annealing S1.2, the first and/or second block is heated to approx. 800° C. and then annealed at this temperature for approx. 150 minutes in a vacuum (<10-5 mbar). In other words, the temperature is maintained for about 150 minutes. In particular, the temperature can then be lowered again to an ambient temperature according to a predetermined scheme to avoid the occurrence of (internal) stresses in the first and/or second block.

The method step of soldering S1 further comprises an optional method step of applying S1.3 the solder.

The method step of applying S1.3 of the solder is executed after the optional method steps of cleaning S1.1 and annealing S1.2. In the method step of applying S1.3 the solder, the solder is applied to the contact surfaces of the first and/or second block. In particular, the solder can be applied to the contact surfaces. For this purpose, the solder may be plate-shaped. In particular, the solder is solid during application.

The method step of soldering S1 may further comprise a method step of joining together S1.5 the first and the second block.

In particular, the first and second blocks are joined together after the solder has been applied. In particular, the first and second blocks may be joined together at their contact surfaces. Alternatively, the first and second blocks can be joined together via a compensating layer 131. In other words, prior to joining S1.5, the compensating layer 131 may be placed between the contact surfaces. The compensating layer 131 is then arranged between the contact surfaces of the first and second blocks. Each of the two contact surfaces is then joined together with the compensating layer 131. In this manner, the first and second blocks are also indirectly joined together. The joined blocks form the combination block. The soldering point 13 is formed by joining S1.5.

In particular, the first and second blocks may be joined together under a vacuum. In particular, the first and second blocks may be joined together at a temperature greater than or equal to a melting point of the solder. In this manner, the solder melts during the joining together and fuses to the contact surfaces of the first and second materials.

The method step of soldering S1 also comprises an optional method step of cooling down S1.6 the combination block.

In particular, the combination block is cooled in a targeted manner along a planned temperature curve. In particular, the combination block is cooled from at least the melting point of the solder to an ambient temperature. In particular, the temperature curve for the cooling down is planned such that magnetization of the first material and/or the second material and/or the material of the compensating layer 131 and/or the solder can be reduced or prevented. In particular, the temperature curve for the cooling down may be planned in such a way that an occurrence of (internal) stresses in the combination block can be reduced or prevented.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element (s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Where not explicitly done, but useful and in the spirit of the invention, individual exemplary embodiments, individual aspects thereof or features can be combined or interchanged without departing from the scope of the present invention. Where transferrable, advantages of the invention described with respect to an exemplary embodiment also apply to other embodiments without explicit mention.

The invention claimed is:

1. A fin for collimating therapeutic radiation comprising:
   a collimation area including a first material;
   a holding area including a second material; and
   a compensating layer between the first material and the second material, the compensating layer including a compensating material configured to compensate for a difference in coefficients of thermal expansion of the first material and the second material, respectively,
   wherein the collimation area and the holding area are soldered together,
   the first material is configured to collimate therapeutic radiation, and
   the holding area is couplable to an adjustment device for adjusting the fin.

2. The fin as claimed in claim 1, wherein the first material and the second material are hard-soldered together.

3. The fin as claimed in claim 2, wherein the first material and the second material are paramagnetic.

4. The fin as claimed in claim 2, wherein the first material is tungsten or a compound comprising tungsten.

5. The fin as claimed in claim 2, wherein the second material comprises titanium or stainless steel.

6. The fin as claimed in claim 1, wherein the first material and the second material are paramagnetic.

7. The fin as claimed in claim 6, wherein the first material is tungsten or a compound comprising tungsten.

8. The fin as claimed in claim 1, wherein the first material is tungsten or a compound comprising tungsten.

9. The fin as claimed in claim 1, wherein the second material comprises titanium or stainless steel.

10. The fin as claimed in claim 1, wherein the holding area and the collimation area are soldered together with a copper solder, a gold solder, a silver solder or a titanium solder.

11. The fin as claimed in claim 1, wherein the compensating layer is formed by a copper plate.

12. The fin as claimed in claim 1, wherein
    the compensating layer is formed by a net-like element and a solder, and
    the net-like element includes nickel.

13. The fin as claimed in claim 1, further comprising:
    a guide element, wherein the guide element is formed by the first material and the second material.

14. A method for manufacturing the fin as claimed in claim 1, the method comprising:
    soldering together a first block including the first material and a second block including the second material to form a combination block.

15. The method as claimed in claim 14, further comprising:
    cutting out the fin from the combination block by wire erosion.

16. The method as claimed in claim 14, further comprising:
    milling out at least one side surface of the fin from the combination block.

17. The method as claimed in claim 14, wherein the soldering includes:
    introducing the compensating layer between contact surfaces of the first block and the second block.

18. The method as claimed in claim 14, further comprising:
    at least one of
    (i) milling out at least one guide element from the combination block, or
    (ii) milling out a contour of the holding area from the combination block.

19. A collimator comprising:
    a plurality of fins, each of the plurality of fins including,
        a collimation area including a first material, a holding area including a second material, and a compensating layer between the first material and the second material, the compensating layer including a compensating material configured to compensate for a difference in coefficients of thermal expansion of the first material and the second material, respectively,
        wherein the collimation area and the holding area are soldered together,
        the first material is configured to collimate therapeutic radiation, and
        the holding area is couplable to an adjustment device for adjusting the fin; and the adjustment device,
wherein the respective holding areas of the fins are coupled to the adjustment device, and
the adjustment device is configured to adjust each fin of the plurality of fins perpendicular to a contact surface of the holding area and the collimation area.

* * * * *